United States Patent [19]

Frame et al.

[11] Patent Number: 5,869,717
[45] Date of Patent: Feb. 9, 1999

[54] PROCESS FOR INHIBITING THE POLYMERIZATION OF VINYL AROMATICS

[75] Inventors: Robert R. Frame, Glenview; Paul R. Kurek, Barrington, both of Ill.

[73] Assignee: UOP LLC, Des Plaines, Ill.

[21] Appl. No.: 932,202

[22] Filed: Sep. 17, 1997

[51] Int. Cl.⁶ .................................................. C07C 7/20
[52] U.S. Cl. .................... 585/5; 585/2; 585/3; 585/4; 585/864; 585/952; 208/48 AA; 203/8; 203/9; 203/57
[58] Field of Search .................................. 585/2, 3, 4, 5, 585/864, 952; 203/8, 9, 57; 208/48 AA

[56] References Cited

U.S. PATENT DOCUMENTS

| | | | |
|---|---|---|---|
| 3,988,212 | 10/1976 | Watson | 203/65 |
| 4,013,580 | 3/1977 | Hayashi et al. | 252/182 |
| 4,050,993 | 9/1977 | Daniels | 203/9 |
| 4,341,600 | 7/1982 | Watson | 203/9 |
| 4,654,451 | 3/1987 | Miller et al. | 585/5 |
| 4,929,778 | 5/1990 | Roling | 585/3 |
| 4,967,027 | 10/1990 | Takahashi et al. | 585/5 |
| 5,034,156 | 7/1991 | Varwig | 252/403 |
| 5,254,760 | 10/1993 | Winter et al. | 585/5 |
| 5,312,952 | 5/1994 | Grossi et al. | 558/46 |
| 5,396,004 | 3/1995 | Arhancet et al. | 585/5 |

FOREIGN PATENT DOCUMENTS

| | | |
|---|---|---|
| 697386-A1 | 2/1996 | European Pat. Off. . |
| 59029624-A | 8/1982 | Japan . |
| 1226858-A | 9/1989 | Japan . |
| 3149205-A | 6/1991 | Japan . |
| 05310815-A | 11/1993 | Japan . |
| 07010910-A | 1/1995 | Japan . |
| WO9503263 | 2/1995 | WIPO . |

*Primary Examiner*—Elizabeth D. Wood
*Attorney, Agent, or Firm*—Thomas K. McBride; Frank S. Molinaro

[57] ABSTRACT

Applicants have developed a process for inhibiting the polymerization of vinyl aromatic compound during the distillation of the vinyl aromatic compounds. The process involves adding to the vinyl aromatic compound, e.g., styrene, a nitroso compound such as N-nitroso-N, N'-di-3-pentyl-p-phenylenediamine.

18 Claims, No Drawings

PROCESS FOR INHIBITING THE POLYMERIZATION OF VINYL AROMATICS

FIELD OF THE INVENTION

This invention relates to a process for inhibiting the polymerization of vinyl aromatic compounds such as styrene during the distillation of said compounds, by adding to the vinyl aromatic compound a nitroso compound such as N-nitroso-N, N'-di-3-pentyl-p-phenylenediamine.

BACKGROUND OF THE INVENTION

Styrene is one of several vinyl aromatic compounds which has considerable commercial utility. Styrene is polymerized into polystyrene which is a clear, readily colored and easily fabricated plastic with many uses. The efficiency of the polymerization process is dependent on the purity of the monomer starting material. Since the processes for producing styrene, and other vinyl aromatic compounds, will contain various reaction products including benzene, toluene, etc., the mixture is distilled to separate these undesirable contaminants. Unfortunately, the temperatures required for distillation, typically 90° C. to about 150° C., leads to the polymerization of the vinyl aromatic compounds. In order to minimize or prevent polymerization of the vinyl aromatic monomer, it is common to add a polymerization inhibitor to the distillation mixture.

The art discloses a variety of compounds which are claimed to inhibit polymerization. These include U.S. Pat. No. 4,050,993 which discloses the use of N,N-nitrosomethylaniline as a polymerization inhibitor. U.S. Pat. No. 3,988,212 which disclose the use of N-nitrosodiphenyl amine in combination with dinitro-o-cresol. U.S. Pat. No. 4,013,580 which discloses the use of N-nitroso aniline derivatives. U.S. Pat. No. 4,341,600 which discloses the use of a mixture of dinitro-p-cresol and N-nitroso-diphenyl amine. U.S. Pat. No. 4,654,451 which discloses alkyl substituted p-nitroso phenol in combination with p-nitroso phenol. U.S. Pat. No. 5,034,156 which discloses N-nitrosophenyl-hydroxylamine plus hydroquinone monomethyl ether. U.S. Pat. No. 5,396,004 which discloses a phenylene-diamine compound plus a hydroxyalkylhydroxyl-amine compound. U.S. Pat. No. 5,254,760 which discloses 1-oxy-2,2,6,6-tetramethylpiperidine plus an aromatic nitro compound. U.S. Pat. No. 4,929,778 which discloses a phenylenediamine compound plus a hindered phenol compound. U.S. Pat. No. 5,312,952 which discloses the use of the reaction product of a $C_9$–$C_{20}$ alkyl phenol with sulfuric and nitric acid and optionally an aryl or alkyl-substituted phenylene-diamine. WO9503263 which discloses 3,5-di-tert-butyl-4-hydroxy-N,N-dimethyl benzyl amine. EP-697386-A2 which discloses 4-acetylamino-2,2,6,6-tetramethyl piperidine N-oxyl in combination with 4-nitroso phenol. JP0701910-A which discloses phosphite compounds, nitrosoamine compounds or phenol compounds. JP05310815-A which discloses the ammonium salt of N-nitrosophenyl hydroxylamine. JP03149205-A which discloses nitrosophenols plus dicyclohexyl-ammonium nitrate. J01226858-A which discloses the use of substituted nitrosobenzene. U.S. Pat. No. 4,967,027 which discloses p-nitroso phenol plus p-t-butyl catechol. J59029624-A which discloses the use of N-nitroso compound, e.g., N-nitroso-diphenylamine and a catechol, e.g., p-t-butylcatechol.

In contrast to these compounds, applicants have found a series of compounds which are particularly effective in inhibiting the polymerization of vinyl aromatic compounds in general and styrene in particular. These compounds are the N-nitroso derivates of unsubstituted or dialkyl substituted phenylenediamine having the following structure:

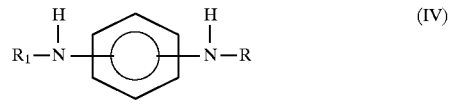

Both the mono and di-nitroso derivates are useful as inhibitors. The compounds can be used by themselves or in combination with the phenylenediamine.

SUMMARY OF THE INVENTION

As stated, this invention relates to a process for inhibiting the polymerization of a vinyl aromatic compound during its distillation. One embodiment of the process involves adding to the vinyl aromatic compound an effective amount of the reaction product of nitrous acid and an amine having the formula:

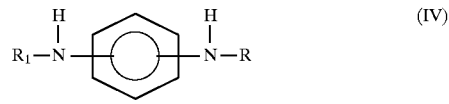

where R and $R_1$ are each hydrogen or an alkyl group having from 1 to 18 carbon atoms.

Another embodiment is a process for inhibiting the polymerization of a vinyl aromatic compound during the distillation of the vinyl aromatic compound comprising adding to the compound an effective amount of a nitroso compound selected from the group consisting of:

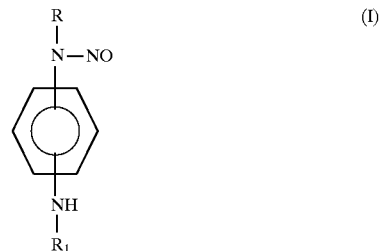

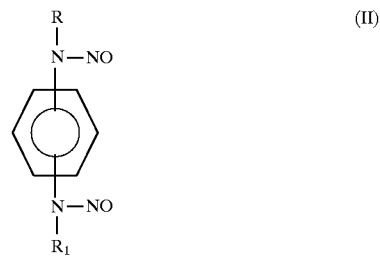

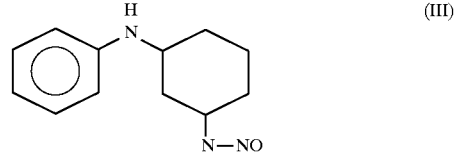

and mixtures thereof where R and $R_1$ are each hydrogen or an alkyl group having from 1 to 18 carbon atoms.

Yet another embodiment is a process for inhibiting the polymerization of a vinyl aromatic compound during the distillation of the vinyl aromatic compound comprising adding to the compound an effective amount of a mixture of inhibitor compounds having structures I, II and IV:

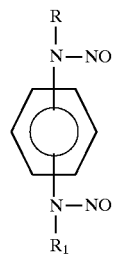

(I)

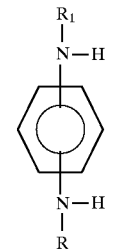

(II)

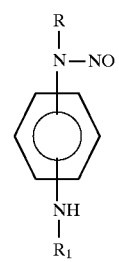

(IV)

where R and R$_1$ are each hydrogen or an alkyl group having from 1 to 18 carbon atoms.

These and other objects and embodiments will become more evident after a detailed description of the invention.

DETAILED DESCRIPTION OF THE INVENTION

The present invention relates to a process for inhibiting the polymerization of a vinyl aromatic compound during its distillation. Vinyl aromatic compounds to which the instant process is applicable include styrene, alpha-methyl styrene, divinylbenzene, vinyl toluene, vinyl naphthalene and polyvinyl-benzene.

The process generally involves adding an inhibitor compound to the vinyl aromatic compound during its distillation. The inhibitor compounds which can be used in the present process include nitroso compounds selected from the group consisting of:

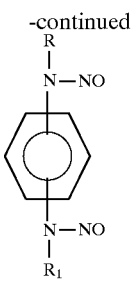

(I)

N-nitroso-dialkyl phenylenediamine

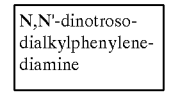

(II)

N,N'-dinotroso-dialkylphenylene-diamine

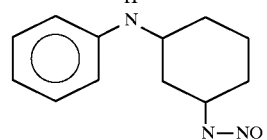

(III)

N-phenyl,N'-nitroso-1,4-diamino cyclohexane

The R and R$_1$ groups can each be hydrogen or an alkyl group having from 1 to 18 carbon atoms. Illustrative of the alkyl groups which can be used are methyl, ethyl, propyl, butyl, pentyl, octyl, decyl, sec-butyl, iso-propyl and isopentyl. Included in structures I and II above are the o, m and p isomers. Preferred compounds encompassed within structures I and II are the following compounds having structure IA and IIA.

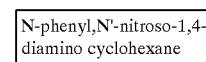

(IA)

N-nitroso-N,N'-di-3-pentyl-p-phenylenediamine

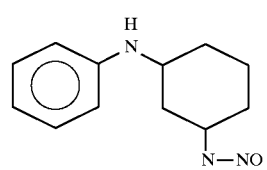

(IIA)

N,N'-dinitroso-N,N'-di-3-pentyl-p-phenylenediamine

Another nitroso compound which can be used as a polymerization inhibitor is N-phenyl, N'-nitroso-1,4-diamino cyclohexane which has structure III below.

(III)

The nitroso compounds are prepared by reacting nitrous acid with an amine. The amine used to obtain these compounds have structures (IV) and (V) below.

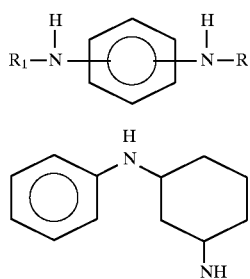

The reaction of nitrous acid with an amine is well known in the art and is included here for completeness. Generally, the amine is reacted with nitrous acid at a temperature of about −10° C. to about 10° C. The nitrous acid can be added or it can be generated in situ by adding sodium nitrite and hydrochloric acid. Further, in the case of a diamine, the amount of nitrous acid added will determine whether the mono or dinitroso compounds are obtained. However, even if a 1:1 stoichiometric amount of nitrous acid:amine is added, a mixture of the mono and dinitroso compounds may still be obtained. Accordingly, the exact nature of the reaction product may not be known. The reaction product may contain both mono and dinitroso compounds along with unreacted amine. In fact, the unreacted amine can act as a solvent for the nitroso compound.

In a preferred embodiment, the amine is N,N'-di-3-pentyl-p-phenylene-diamine which is represented by structure (IVA) below.

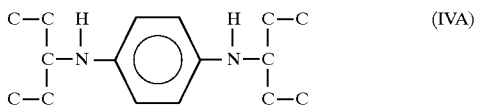

The reaction product may contain compounds IA, IIA and IVA.

It is, therefore, one embodiment of the present invention to use the reaction product described above as the polymerization inhibitor. Alternatively, the pure components can be isolated and used either individually or in combination with each other. The separate components can be isolated by means well known in the art such as fractional crystallization, liquid chromatography and column chromatography.

In order to adequately prevent polymerization of the vinyl aromatic compounds, an effective amount of the nitroso compound or mixtures thereof must be used. For the nitroso compound having structures I and III, an effective amount varies from about 1 to about 1000 ppm. If the nitroso compound has structure (II), then the effective amount varies from about 1 to about 1000 ppm. When mixtures of compounds (I) (II) and (IV) are used the amounts of each component in the mixture varies as follows: compound I varies from about 18 to about 96 wt. %, compound II varies from 2 wt. % to about 50 wt. % and compound IV varies from about 2 wt. % to about 80 wt. %. The amount of the mixture which is added to the vinyl aromatic compound varies from about 1 to about 1000 ppm.

As has been stated, the reaction product of the amine and nitrous acid can be used as is without further purification. Thus when the amine is represented by structure IV, the reaction product may contain compounds I, II, IV plus other compounds and the amount of the reaction product which is added to the vinyl aromatic compound varies from about 1 to about 1000 ppm.

Having added the effective amount of inhibitor to the mixture containing the vinyl aromatic compound, the mixture is distilled at a temperature of about 65° C. to about 150° C. in standard distillation columns. The distillation temperature can be controlled by controlling the pressure in the column from about 1 kPa to about 53 kPa. Further, the inhibitor may be added to the vinyl aromatic compound in any convenient manner. Usually the inhibitor is added in liquid form by periodically or continuously adding the required amount to the inlet distillation feed. In this respect, if the inhibitor is a solid, it is dissolved in an appropriate solvent. Illustrative of the solvents which can be used are toluene, benzene, ethylbenzene, xylenes, etc. Preferred solvents are ethylbenzene or the starting amine which allows for easy separation from the purified vinyl aromatic compound.

The following examples are presented in illustration of the invention and are not intended as undue limitations in the generally broad scope of the invention as set out in the appended claims.

EXAMPLE 1

In a round bottom flask, there were placed 2.1 g of N,N'-di-3-pentyl-p-phenylenediamine obtained from UOP and identified as UOP No. 5®. To this flask, which was chilled to 0° C., there were added 50 mL of a hydrochloric acid solution composed of equal parts water and concentrated hydrochloric acid. Next a solution of 0.51 g sodium nitrite in 12 mL of water were added over a twenty minute period. Any excess acid was now neutralized with a chilled solution of sodium hydroxide. The resultant mixture was poured into a separatory funnel to which there were added 100 mL of ethyl ether. The organic phase was collected, dried and the ethyl ether removed by use of a rotary evaporator. The isolated product was a dark colored liquid which was identified as sample A.

EXAMPLE 2

The following test procedure was used to determine the ability of sample A to inhibit the polymerization of styrene. Five glass ampules were filled with 5 g of styrene and a given amount of sample A. Four ampules were placed in an oil bath heated to 120° C. The fifth ampule was analyzed to give the initial amount of polymerization. One ampule was removed at 1 hour increments and the contents filtered to determine the amount of polystyrene which was formed. These results are presented in The Table below. As a comparison, dinitro-butyl-phenol (DNBP) and dinitro-phenol (DNP) were also tested in the same manner and those results are also presented in the Table.

THE TABLE

Polymerization Inhibitor Activity of Various Inhibitors

| | % Polymerization | | | | |
|---|---|---|---|---|---|
| Sample I.D. | Initial | 1 hour | 2 hours | 3 hours | 4 hours |
| Sample A (250 ppm) | 0 | 0 | 0 | 0 | 0 |
| Sample A (175 ppm) | 0 | 0 | 0.3 | 0.1 | 1.3 |
| Sample A (125 ppm) | 0 | 0 | 0.5 | 0.1 | 6.3 |
| Sample A (75 ppm) | 0 | 0.1 | 0 | 10.3 | 14.2 |
| DNBP (500 ppm) | 0 | 0.1 | 0.5 | 1.5 | — |
| DNBP (300 ppm) | 0 | 0 | 1 | 2 | 3.6 |
| DNP (500 ppm) | 0 | 0.2 | 0.5 | 0.8 | — |
| DNP (300 ppm) | 0 | 0.5 | 0.9 | 1.5 | |

The data in The Table show that the inhibitors of the present invention have superior activity to inhibitors of the prior art. The instant inhibitors have the same activity as DNBP or DNP but at one third the concentration.

We claim as our invention:

1. A process for inhibiting the polymerization of a vinyl aromatic compound during distillation of the vinyl aromatic compound comprising adding to the compound an effective amount of the reaction product of nitrous acid and an amine having the formula:

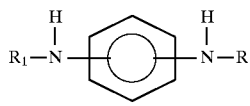

where R and $R_1$ are each hydrogen or an alkyl group having from 1 to 18 carbon atoms.

2. The process of claim 1 where R and $R_1$ are each selected from the group consisting of hydrogen, methyl, ethyl, propyl, butyl, pentyl, sec-butyl, iso-propyl and iso-pentyl.

3. The process of claim 2 where the amine is

4. The process of claim 1 where the reaction product is present in an amount from about 1 to about 1000 ppm.

5. The process of claim 1 where the vinyl aromatic compound is selected from the group consisting of styrene, alpha-methyl styrene, divinylbenzene, vinyl toluene, vinyl naphthalene and polyvinylbenzene.

6. A process for inhibiting the polymerization of a vinyl aromatic compound during the distillation of the vinyl aromatic compound comprising adding to the compound an effective amount of a nitroso compound selected from the group consisting of:

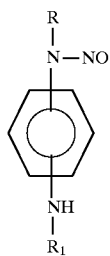

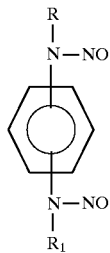

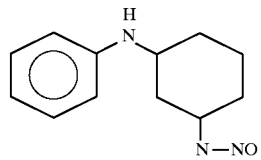

and mixtures thereof and R and $R_1$ are each hydrogen or an alkyl group having from 1 to 18 carbon atoms.

7. The process of claim 6 where the nitroso compound is

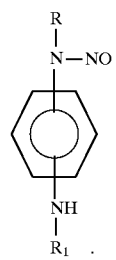

8. The process of claim 6 where the nitroso compound is

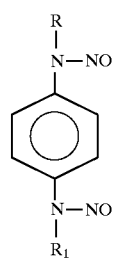

9. The process of claim 6 where the nitroso compound is present in an amount from about 1 to about 1000 ppm.

10. The process of claim 6 where the nitroso compound is a mixture of compound I and II.

11. The process of claim 6 where R and $R_1$ are each selected from the group consisting of hydrogen, methyl, ethyl, propyl, butyl, pentyl, sec-butyl, iso-propyl and iso-pentyl.

12. The process of claim 7 where the nitroso compound is

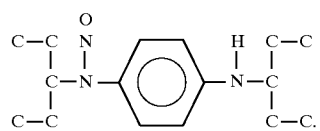

13. A process for inhibiting the polymerization of a vinyl aromatic compound during the distillation of the vinyl aromatic compound comprising adding to the compound an effective amount of a mixture of inhibitor compounds having structures I, II and IV:

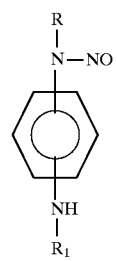

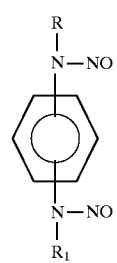

-continued

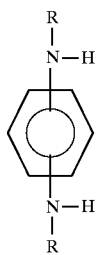
(IV)

where R and R₁ are each hydrogen or an alkyl group having from 1 to 18 carbon atoms.

14. The process of claim 13 where the amount of compound I varies from about 18 to about 96 wt. %, the amount of compound II varies from 2 wt. % to about 50 wt. % and the amount of compound IV varies from 2 wt. % to about 80 wt. %.

15. The process of claim 13 where the amount of the mixture present varies from about 1 to about 1000 ppm.

16. The process of claim 13 where R and R₁ are each selected from the group consisting of hydrogen, methyl, ethyl, propyl, butyl, pentyl, sec-butyl, iso-propyl and iso-pentyl.

17. The process of claim 13 where compounds I, II and IV have structures IA, IIA and IVA:

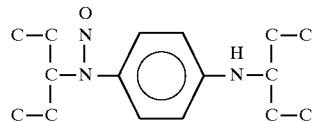
(IA)

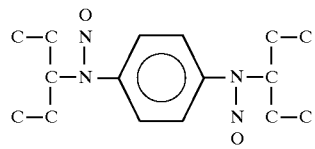
(IIA)

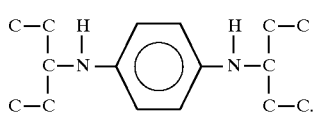
(IVA)

18. The process of claim 13 where the vinyl aromatic compound is selected from the group consisting of styrene, alpha-methyl styrene, divinylbenzene, vinyl toluene, vinyl naphthalene and polyvinylbenzene.

* * * * *

UNITED STATES PATENT AND TRADEMARK OFFICE
CERTIFICATE OF CORRECTION

PATENT NO: 5,869,717
DATED: Feb. 9, 1999
INVENTOR(S): Frame, et al.

It is certified that error appears in the above-identified patent and that said Letters Patent is hereby corrected as shown below:

In claim 13, column 9, line 2, "R" should be "$R_1$".

Signed and Sealed this

Thirty-first Day of August, 1999

Attest:

Q. TODD DICKINSON

Attesting Officer

Acting Commissioner of Patents and Trademarks